United States Patent [19]

Uemura et al.

[11] Patent Number: 5,054,495
[45] Date of Patent: Oct. 8, 1991

[54] AUTOMATIC BLOOD-PRESSURE MEASURING APPARATUS

[75] Inventors: Masahiro Uemura, Komaki; Hideichi Tsuda, Kasugai; Hifumi Yokoe, Kosai; Tokuji Hayakawa, Komaki, all of Japan

[73] Assignee: Colin Electronics Co., Ltd., Aichi, Japan

[21] Appl. No.: 377,566

[22] Filed: Jul. 10, 1989

[51] Int. Cl.$^5$ .......................................... A61B 5/0225
[52] U.S. Cl. ..................................... 128/680; 128/677
[58] Field of Search ......................... 128/672, 677–686

[56] References Cited

U.S. PATENT DOCUMENTS

| | | | |
|---|---|---|---|
| 3,905,354 | 9/1975 | Lichowsky | 128/681 |
| 4,459,991 | 7/1984 | Hatschek | 128/681 |
| 4,729,383 | 3/1988 | Susi | 128/681 |
| 4,796,184 | 1/1989 | Bahr et al. | 128/681 X |
| 4,840,181 | 6/1989 | Yamaguchi | 128/681 |
| 4,850,368 | 7/1989 | Miyawaki | 128/683 |
| 4,870,973 | 10/1989 | Ueno | 128/680 |
| 4,880,013 | 11/1989 | Chio | 128/681 |

Primary Examiner—Lee S. Cohen
Assistant Examiner—K. M. Pfaffle
Attorney, Agent, or Firm—Oliff & Berridge

[57] ABSTRACT

An apparatus for automatically measuring a blood pressure of a subject, including a pressing device for pressing a body portion of the subject, such as an upper arm; a first blood pressure measuring device for detecting pulse sounds which are produced from the body portion as the pressing force of the pressing device is varied, and determining a first blood pressure (BP) value of the subject based on at least one of an appearance and a disappearance of the pulse sounds; a second blood pressure measuring device for detecting an oscillatory pressure wave which is produced from the body portion in synchronization with heartbeat of the subject as the pressing force of the pressing device is varied, and determining a second BP value of the subject based on variation in magnitude of the oscillatory pressure wave; and a judging device for judging at least one of the first and second blood pressures to be abnormal if a degree of inequality between the first and second blood pressures exceeds a reference value.

9 Claims, 3 Drawing Sheets

AUTOMATIC BLOOD-PRESSURE MEASURING APPARATUS

BACKGROUND OF THE INVENTION

1. Field of the Invention

The present invention relates in general to an automatic blood pressure measuring apparatus, and in particular to such an apparatus which provides blood pressure measurements or values with improved reliability.

2. Discussion of the Prior Art

There are generally known two types of automatic blood pressure measuring systems which automatically measure a blood pressure (BP) of a living body while pressing a limb or other body portion of the subject with a pressing device such as an inflatable cuff. The automatic BP measuring system of the K-sound type, as one of the two types, includes a sensor for detecting pulse sounds (Korotkoff sounds or "K sounds") produced from the pressed body portion of the subject as the pressing force of the pressing force is varied, and determines a BP value of the subject based on appearance and/or disappearance of the K sounds. The other known automatic BP measuring system of the oscillometric type is adapted to detect an oscillatory pressure wave (pulse wave) produced from the pressed body portion of the subject in synchronization with a noise-mixed pulsation of the heart (heartbeat) of the subject as the pressing force is varied, and determines a BP value of the subject based on variation in magnitude of the pulse wave.

However, the above K sound-type system suffers from a problem of detecting noises, such as sounds caused by rustling of clothes of the subject, mixed with the K sounds. Similarly, the above oscillometric-type system suffers from a problem of detecting noises, such as a pressure wave acting on the pressing device as a result of bending of the elbow or arm of the subject, mixed with the oscillatory pressure wave or pulse wave. The thus measured BP values are not sufficiently reliable, since those values are determined based on the K sounds and/or pulse wave detected with possibility of the noise mixture therewith. That is, the K sound-type system alone, or the oscillometric-type system alone is not sufficiently reliable.

SUMMARY OF THE INVENTION

It is therefore an object of the present invention to provide an automatic blood pressure measuring apparatus which provides blood pressure measurements or values with improved reliability.

The above object has been achieved by the present invention, which provides an automatic blood pressure measuring apparatus for automatically measuring a blood pressure of a subject, comprising (a) a pressing device for pressing a body portion of the subject, (b) first blood pressure measuring means for detecting pulse sounds which are produced from the body portion as the pressing force of the pressing device is varied, and determining a first blood pressure of the subject based on at least one of an appearance and a disappearance of the pulse sounds, (c) second blood pressure measuring means for detecting oscillatory pressure wave which is produced from the body portion in synchronization with heartbeat of the subject as the pressing force is varied, and determining a second blood pressure of the subject based on variation in magnitude of the oscillatory pressure wave, and (d) judging means for judging at least one of the first and second blood pressures to be abnormal if a degree of inequality between the first and second blood pressures exceeds a reference value.

In the automatic BP measuring apparatus of the present invention constructed as described above, the first and second BP measuring means determine a first and a second BP value of the subject as the pressing force of the pressing device is varied, and the judging means judges at least one of the first and second BP values to be abnormal if a degree of inequality between the first and second BP values exceeds a reference value. That is, the present apparatus is capable of judging the abnormality of the BP values determined based on the noise-mixed K sounds and/or pulse wave. Accordingly, the present apparatus provides BP values with increased reliability.

According to a feature of the present invention, the first and second blood pressure measuring means automatically determine another first blood pressure and another second blood pressure, respectively, if the judging means judges the at least one of the first and second blood pressures to be abnormal.

In a preferred embodiment of the apparatus of the present invention, the pressing device comprises an inflatable cuff which is inflated by pressurized fluid supplied thereto, the pressing device pressing the body portion of the subject by increasing a fluid pressure in the inflatable cuff to a predetermined value which is higher than an estimated maximum blood pressure of the subject and subsequently decreasing the fluid pressure.

In the above embodiment, the first and second blood pressure measuring means may determine the first and second blood pressures, respectively, as the fluid pressure of the cuff is progressively decreased from the predetermined value. In this case, the first blood pressure measuring means may determine, as a maximum blood pressure of the subject, a value of the fluid pressure when the pulse sounds appears to be detected thereby, determines as a minimum blood pressure of the subject a value of the fluid pressure when the pulse sounds disappears subsequent to the appearance thereof, determines an average blood pressure based on the maximum and minimum blood pressure, one of the maximum, minimum and average blood pressure being used as the first blood pressure. Similarly, the second blood pressure measuring means may determine, as a maximum blood pressure of the subject, a value of the fluid pressure when amplitudes of pulses of the oscillatory pressure wave are significantly largely increased, determines as a minimum blood pressure of the subject a value of the fluid pressure when the amplitudes of the pulses are significantly largely decreased subsequent to the significantly large increase, and determines an average blood pressure based on the maximum and minimum blood pressures, one of the maximum, minimum and average blood pressures being used as the second blood pressure.

In another embodiment of the apparatus of the present invention, a difference between the first and second blood pressures is used as the degree of inequality between the first and second blood pressures, the reference value being determined based on a maximum difference among the differences between the first blood pressures and the corresponding second blood pressures which are determined by the first and second blood pressure measuring means, respectively, while the subject is in a normal condition.

In yet another embodiment of the present invention, the apparatus further comprises a display device for displaying, as a normal blood pressure, a value determined based on at least one of the first and second blood pressures, unless the judging means judges the at least one of the first and second blood pressures to be abnormal. Also, the display device may display an indication of abnormality, if the judging means judges the at least one of the first and second blood pressures to be abnormal.

BRIEF DESCRIPTION OF THE DRAWINGS

The above and optional objects, features and advantages of the present invention will be better understood by reading the following detailed description of a presently preferred embodiment of the invention, when considered in conjunction with the accompanying drawings, in which.

DETAILED DESCRIPTION OF THE PREFERRED EMBODIMENT

Figure 1:
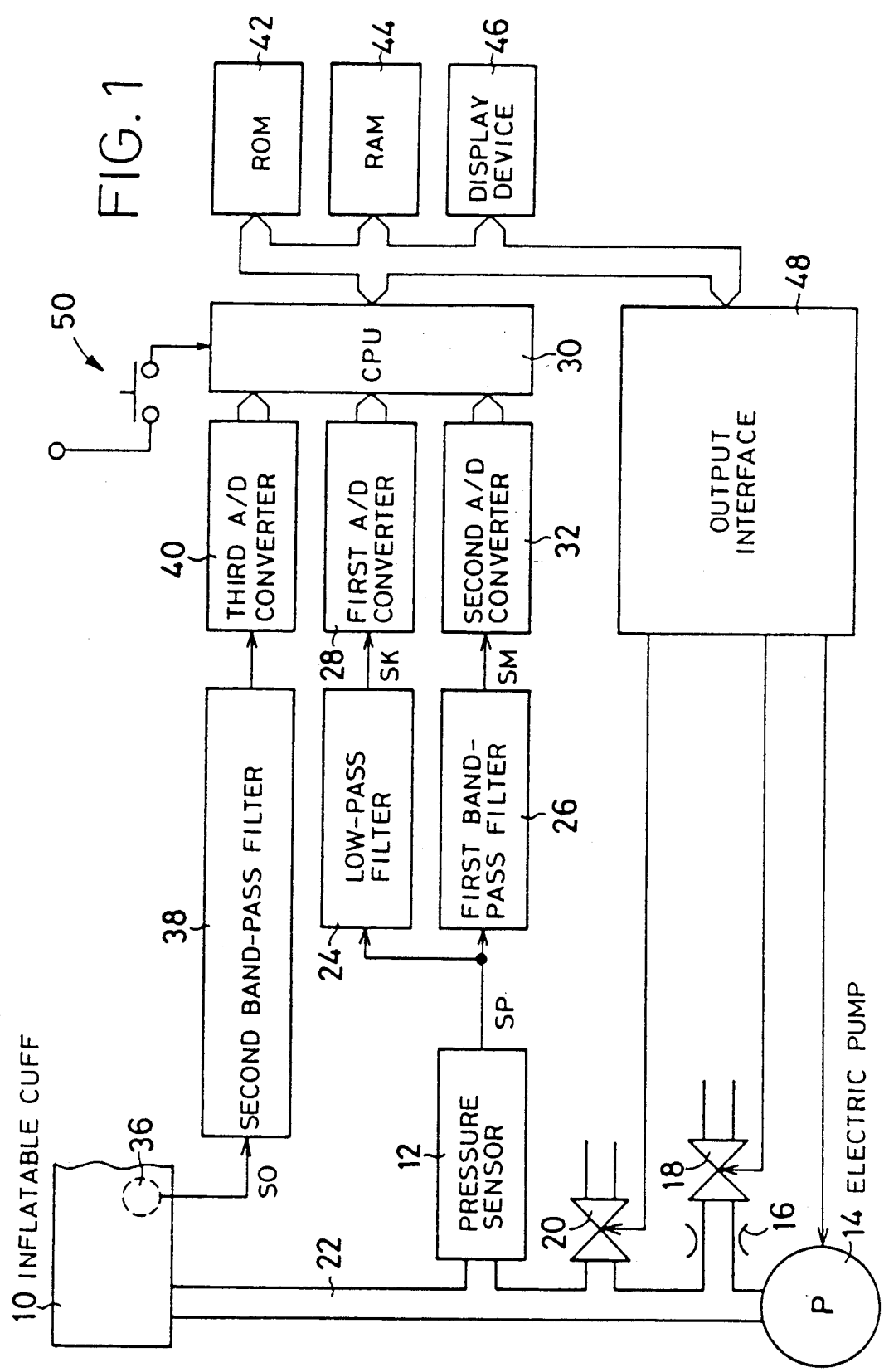
FIG. 1 is a diagrammatic view illustrating the arrangement of an automatic blood pressure measuring apparatus of the present invention.

Referring to FIG. 1 there is illustrated an automatic blood pressure measuring apparatus embodying the present invention. Reference numeral 10 designates a pressing device in the form of an inflatable cuff which is wound around an upper arm of a living body. The inflatable cuff 10 is associated via a piping 22 with a pressure sensor 12, an electric pump 14, a slow-deflation valve 18 with a restrictor 16, and a rapid-deflation valve 20. The inflatable cuff 10 is supplied with pressurized air by the electric pump 14. The pressure sensor 12 detects an air pressure in the cuff 10, and supplies to a low-pass filter 24 and a first band-pass filter 26 a pressure signal SP representing time-wise variation in the air pressure of the cuff 10. Upon reception of signal SP from the pressure sensor 12, the low-pass filter 24 selectively transmits a signal SK representing static pressure in the cuff 10 (hereinafter, referred to as "cuff pressure"). Cuff-pressure signal SK is supplied to a central processing unit (CPU) 30 via a first analog/digital (A/D) converter 28. Meanwhile, upon reception of pressure signal SP, the first band-pass filter 26 selectively transmits frequency components in the range of about 0.1 to 10 Hz., as a pulse-wave signal SM representing the pulse wave applied to the cuff 10. Pulsewave signal SM is supplied to the CPU 30 via a second A/D converter 32. The pulse wave is an oscillatory pressure wave which is transmitted to the cuff 10 in synchronization with pulsation of the heart (heartbeat) of the subject. In the present embodiment, the pressure sensor 12 and the first band-pass filter 26 cooperate with each other to serve as a pulse-wave sensor for detecting the pulse wave.

A microphone 36 is disposed within the inflatable cuff 10. The microphone 36 detects pulse sounds (Korotkoff sounds; hereinafter, referred to as "K sounds" when appropriate) produced from the upper arm of the subject, and supplies a pulse-sound signal SO representing the detected pulse sounds, to a second band-pass filter 38. Upon reception of pulse-sound signal SO from the microphone 36, the second band-pass filter 38 selectively transmits frequency components in the range of about 30 to 80 Hz. Pulse-sound signal SO is supplied to the CPU 30 via a third A/D converter 40. In the present embodiment, the microphone 36 serves as a pulse-sound sensor for detecting the pulse sounds.

The CPU 30 is connected via data bus to a read-only memory (ROM) 42, a random access memory (RAM) 44, a display device 46, and an output interface 48. The CPU 30 processes the received signals SK, SM, SO according to software programs pre-stored in the ROM 42 by utilizing the temporary-storage function of the RAM 44, and controls the operation of each of the electric pump 14, slow-deflation valve 18 and rapid-deflation valve 20 via the output interface 48. Further, the CPU 30 commands implementation of operations for performing a blood pressure (BP) measurement. More specifically described, the CPU 30 operates to determine a pair of BP values of the subject by the oscillometric and K-sound method, respectively. The "oscillometric" BP value is determined based on pulse-wave signal SM and cuff-pressure signal SK, while the "K-sound" BP value is determined based on pulse-sound signal SO and cuff-pressure signal SK. Both of the oscillometric and K-sound BP values are displayed on the display device 46.

Figure 2:
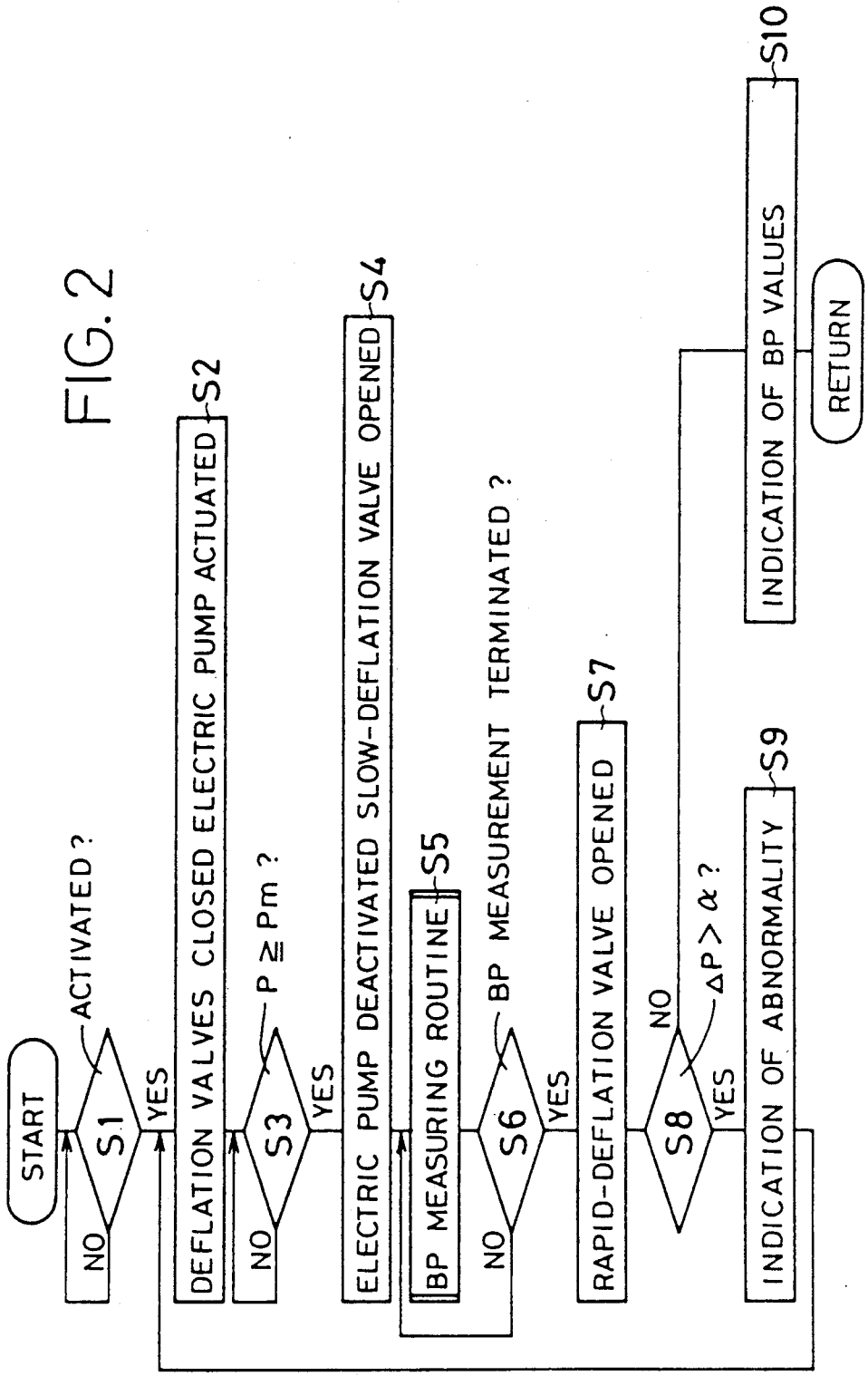
FIG. 2 is a flow chart illustrating the operations of the automatic BP measuring apparatus of FIG. 1.
Figure 3:
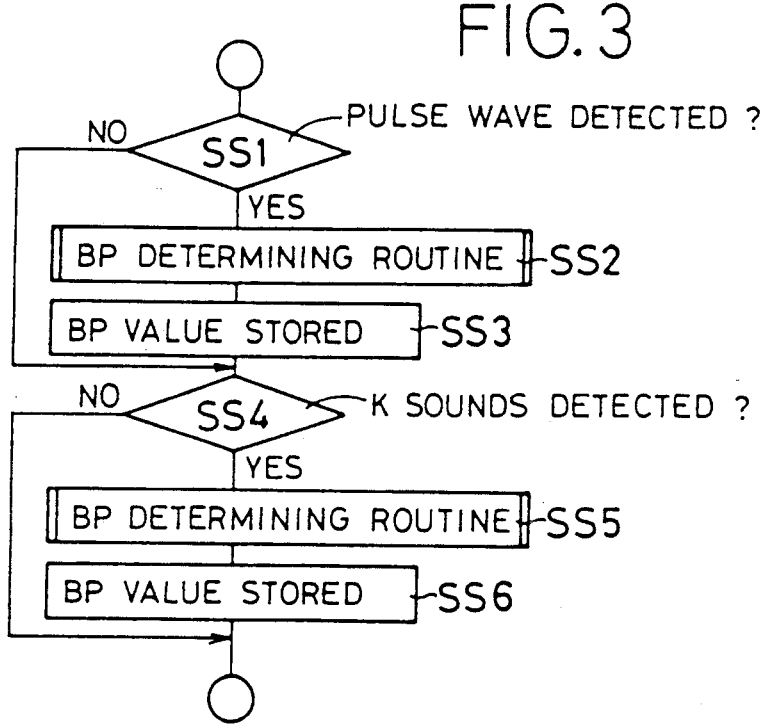
FIG. 3 is a flow chart illustrating the BP measuring routine of the flow chart of FIG. 2.

The automatic BP measuring apparatus constructed as described above, is operated according to the flow charts of FIGS. 2 and 3.

Initially, upon application of electric power to the instant apparatus, the control of the CPU 30 starts with step S1 of FIG. 2, in which it is judged whether or not a START switch 50 (FIG. 1) has been operated. In the case where the judgement is negative (NO), namely, if the START switch 50 has not been operated yet, step S1 is repeated until the START switch 50 is operated. On the other hand, in the case where the judgement is affirmative (YES), namely, if the START switch 50 has been operated, the control of the CPU 30 goes to step S2 in which both the slow- and rapid-deflation valves 18, 20 are placed in a closed position and the electric pump 14 is activated to supply the inflatable cuff 10 with pressurized air, namely, increase cuff pressure P. Step S2 is followed by step S3 in which it is judged whether or not cuff pressure P has been increased to a predetermined target value Pm which is sufficiently higher than an estimated maximum BP value of the subject, for example 180 mmHg. If the judgement at step S3 is negative, namely, if it is judged that cuff pressure P has not reached target value Pm, step S3 is repeated until cuff pressure P reaches target value Pm. On the other hand, if the judgement at step S3 is affirmative, the control of the CPU 30 goes to step S4 in which the electric pump 14 is deactivated and the slow-deflation valve 18 is placed in an open position, so that cuff pressure P is progressively decreased at a predetermined rate, for example 3 mmHg/sec, which is appropriate for the BP measurement. Step S4 is followed by the BP measuring routine of step S5, in which a maximum and a minimum BP value of the subject are measured by each of the oscillometric and K-sound methods, as cuff pressure P is decreased.

FIG. 3 shows the flow chart corresponding to step S5 of FIG. 2. The control of the CPU 30 effects step SS1 in which it is judged whether or not the pulse wave has been detected, namely, pulse-wave signal SM is present at the CPU 30. If the judgement is negative, the control of the CPU 30 skips steps SS2 and SS3 and goes to step SS4. On the other hand, if the judgement in step SS1 is affirmative, then step SS2 is effected, in which a maximum and a minimum BP value of the subject are determined by the oscillometric method. More specifically described, a value of cuff pressure P measured at a time when the amplitudes of pulses of the pulse wave are significantly largely increased, is determined as a maximum BP value of the subject, while a value of cuff pressure P when the amplitudes of the pulses are significantly largely decreased subsequent to the significantly large increase, is determined as a minimum BP value of the subject. The CPU 30 reads those cuff-pressure values from cuff-pressure signal SK which is time-wise supplied thereto together with pulse-wave signal SM. Step SS2 is followed by step SS3 in which the determined maximum and minimum BP values are stored in the RAM 44. In the present invention, the pressure sensor 12, first band-pass filter 26, step SS2, CPU 30 and others cooperate with each other to serve as the means for determining a BP value of the subject by utilizing the pulse wave.

Subsequently, the control of the CPU 30 goes to step SS4 in which it is judged whether or not the K sounds (pulse sounds) have appeared to be detected, namely, pulse-sound signal SO is present at the CPU 30. If the judgement is negative, the control of the CPU 30 skips steps SS5 and SS6 and advances to step S6 of FIG. 2. On the other hand, if the judgement is affirmative, then step SS5 is effected, in which a maximum and a minimum BP value of the subject are measured by the K-sound method. More specifically described, a value of cuff pressure P measured at a time when the K sounds appears to be detected, is determined as a maximum BP value of the subject, while a value of cuff pressure P when the K sounds disappears subsequent to the appearance, is determined as a minimum BP value of the subject. As described above, the CPU 30 reads those cuff-pressure values from cuff-pressure signal SK time-wise supplied thereto together with pulse-sound signal SO. Step SS5 is followed by step SS6 in which the determined maximum and minimum BP values are stored in the RAM 44. In the present invention, the microphone 36, second band-pass filter 38, step SS5, CPU 30 and others cooperate with each other to serve as the means for determining a BP value of the subject by utilizing the K sounds.

Step S5 (or step SS6) is followed by step S6 in which it is judged whether or not the maximum and minimum BP values of the subject have been determined by each of the oscillometric and K-sound methods. At an early stage in a measuring cycle, the judgement in step S6 is negative, and step S5 and S6 are repeated. On the other hand, if the judgement is turned affirmative, then the control of the CPU 30 goes to step S7 in which the rapid-deflation valve 20 is placed in an open position, so as to decrease cuff pressure P at a high rate.

Step S7 is followed by step S8 in which it is judged whether or not a degree of inequality between the "oscillometric" BP value determined in step SS2, and the "K-sound" BP value determined in step SS5, exceeds a reference value $\alpha$. For example, a difference $\Delta P$ between the "oscillometric" and "K-sound" maximum BP values is utilized as the above-indicated degree of inequality, and is compared with reference value $\alpha$. As reference value $\alpha$, is used a maximum difference of the differences between the maximum BP values determined by the oscillometric method, and the corresponding BP values determined by the K-sound methods, in a plurality of measuring cycles while the subject is in a normal condition free from noises such as those caused by rustling of clothes or bending of the arm. If the judgement is affirmative, namely, if difference $\Delta P$ is greater than reference $\alpha$, it is concluded that at least one pair of the pair of "oscillometric" maximum and minimum BP values and the pair of "K-sound" maximum and minimum BP values, is abnormal. In this case, the control of the CPU 30 goes to step S9 in which the CPU 30 commands the display device 46 to display an indication of abnormality, and not to display BP values of the subject. Step S9 is followed by step S2 and the following steps so as to perform another BP measurement by the oscillometric and K-sound methods. In the present embodiment, step S8, a portion of the ROM 42 storing the program of step S8, the RAM 44 storing the determined maximum and minimum BP values, the CPU 30, and others cooperate with each other to serve as the judging means.

On the other hand, if it is judged at step S8 that difference $\Delta P$ is not greater than reference it is concluded that both of the above-indicated two pairs of maximum and minimum BP values are normal. In this case, the control of the CPU 30 goes to step S10 in which the CPU 30 commands the display device 48 to display the two pairs of maximum and minimum BP values. Alternatively, the display device 48 may be adapted to display a pair of average maximum and minimum BP values which are determined based on the above-indicated two pairs of maximum and minimum BP values.

As is apparent from the foregoing, if noises caused by physical action of the subject, friction of the cuff 10 or the like, are mixed with the pulse wave and/or K sounds in the oscillometric and K-sound methods, difference $\Delta P$ between the two BP values determined based on the noise-mixed pulse wave and/or K sounds may exceed reference value $\alpha$, i.e., the maximum difference among the differences between the "oscillometric" BP values and the corresponding "K-sound" BP values which are determined while the subject is in a normal condition free from such noises. In the case where difference $\Delta P$ exceeds reference value $\alpha$, it is judged in step S8 that at least one of the above-indicated two BP values is abnormal, and in step S9 an indication of abnormality (e.g., "ERROR") is displayed. Further, another measuring cycle is initiated to measure another pair of BP values by the oscillometric and K-sound methods. Thus, the instant automatic BP measuring apparatus is capable of measuring BP values with improved reliability.

While the present invention has been described in detail in the presently preferred embodiment for illustrative purposes only, it is to be understood that the invention is by no means limited to the details of the illustrated embodiment, but may be otherwise embodied.

For example, while in the illustrated embodiment the judgement of abnormality of at least one of the "oscillometic" and "K-sound" BP values determined in a BP measuring cycle, is made by utilizing the maximum BP values determined by the two methods, it is possible to use the minimum BP values, or the average BP values determined based on the maximum and minimum BP values.

Figure 4:
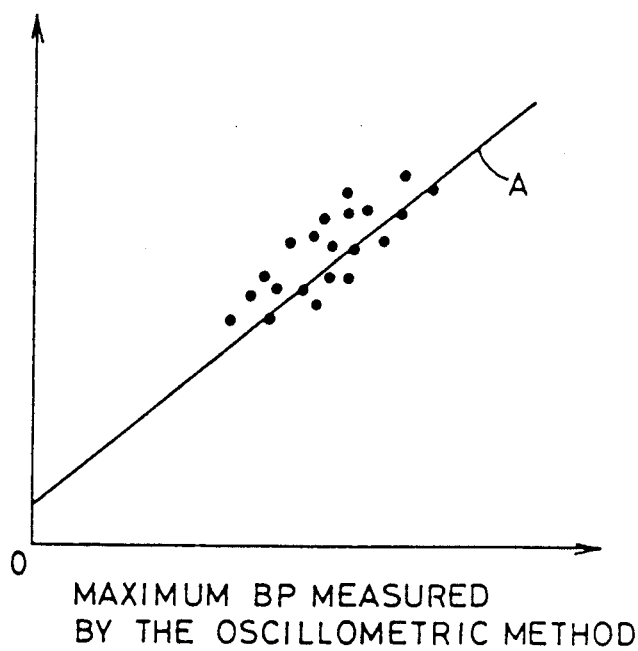
FIG. 4 is a graph showing a correlation between the BP values determined by the oscillometric method and the BP values determined by the K-sound method.

Further, in place of difference ΔP, it is possible to use a statistically determined value as the degree of inequality between the "oscillometric" and "K-sound" BP values. For example, as shown in FIG. 4, a multiplicity of points each of which represents "oscillometric" and "K-sound" maximum BP values measured during an appropriate period of time, are plotted on a two-dimensional table defined by an x-axis indicative of the maximum BP measured by the oscillometric method and a y-axis indicative of the maximum BP measured by the K-sound method, and a regression line A of the multiple points is determined. In this case, a distance between regression line A, and a point M plotted in the table which point represents "oscillometric" and "K-sound" maximum BP values determined in a BP measuring cycle, is used as the degree of inequality of the "oscillometric" and "K-sound" BP values, and compared with a reference value which is calculated based on a standard deviation o of the multiple points with respect to the foot of perpendicular of point M on regression line A. Alternatively, a distance between regression line A and point M as viewed in a direction parallel to the x (or y) axis, may be used as the degree of inequality of the "oscillometric" and "K-sound" BP values, and compared with a reference value which is calculated based on a standard deviation o of the x (or y) coordinates of the multiple points with respect to a point on regression line A which point has the same y (or x) coordinate as that of point M. In either case, if a degree of inquality between the two maximum BP values represented by point M, exceeds a reference value, it is judged that at least one of the two maximum BP values is abnormal, as in the illustrated embodiment.

Moreover, in the illustrated embodiment, if it is judged in step S8 that at least one of the BP values determined by the oscillometric and K-sound methods is abnormal, in step S9 an indication of abnormality is displayed on the display device 46, and subsequently step S2 and the following steps are effected to automatically implement another BP measuring cycle. However, it is possible to adapt the illustrated apparatus to effect only one of the display of the indication of abnormality, and the automatic measurement of another pair of "oscillometric" and "K-sound" BP values.

Furthermore, even in the case of the judgement of abnormality in step S8, it is possible in step S9 to display a normal BP value if one of the "oscillometric" and "K-sounds" BP values is normal. For example, if one of the two BP values has only a significantly small variation with respect to the BP values determined in the two measuring cycles preceding and following the present measuring cycle, as compared with the other of the two BP values, then the one BP value is regarded as a normal value. Alternately, a normal BP value may be found by a statistical method in which, if one of the "oscillometric" and "K-sound" BP values has only a significantly small variation with respect to the moving average of the BP values determined in a predetermined number of consecutive measuring cycles including the present measuring cycle, as compared with the other of the two BP values, then the one BP value is regarded as a normal value.

Furthermore, while in the illustrated embodiment BP values of the subject are determined while cuff pressure P is progressively decreased, it is possible to determine those values while cuff pressure P is progressively increased at a suitable rate.

It is to be understood that the present invention may be embodied with various other modifications, improvements and changes that may occur to those skilled in the art without departing from the spirit and scope of the invention defined in the appended claims.

What is claimed is:

1. An automatic blood pressure measuring apparatus for automatically measuring a blood pressure of a subject having a heartbeat, comprising:
   a pressing device including an inflatable cuff for pressing a body portion of said subject;
   detecting means for detecting a pressure in said cuff;
   first blood pressure measuring means for detecting pulse sounds which are produced from said body portion as the pressure of said cuff is varied, and determining as a first blood pressure of said subject a pressure of said cuff detected by said detecting means at a time of detection of at least one of an appearance and a disappearance of said pulse sounds;
   second blood pressure measuring means for detecting an oscillatory pressure wave which is produced from said body portion and transmitted to said cuff in synchronization with said heartbeat of said subject as the pressure of said cuff is varied, and determining as a second blood pressure of said subject a pressure of said cuff detected by said detecting means at a time of detection of a significantly large variation in amplitude of said oscillatory pressure wave; and
   judging means for judging at least one of said first and second blood pressures to be abnormal if a degree of inequality between said first and second blood pressures exceeds a reference valve.

2. The apparatus as set forth in claim 1, wherein said first and second blood pressure measuring means automatically determine another first blood pressure and another second blood pressure, respectively, if said judging means judges said at least one of the first and second blood pressures to be abnormal.

3. The apparatus as set forth in claim 1, wherein said inflatable cuff is inflated by a pressurized fluid supplied thereto, said pressing device pressing said body portion of said subject by increasing a fluid pressure in said inflatable cuff to a predetermined value which is higher than an estimated maximum blood pressure of said subject and subsequently decreasing said fluid pressure.

4. The apparatus as set forth in claim 3, wherein said first and second blood pressure measuring means determine said first and second blood pressures, respectively, as said fluid pressure of the cuff is progressively decreased from said predetermined value.

5. The apparatus as set forth in claim 4, wherein said first blood pressure measuring means determines, as a maximum blood pressure of said subject, a value of said fluid pressure when said pulse sounds appear to be detected thereby, determines as a minimum blood pressure of said subject a value of said fluid pressure when said pulse sounds disappear subsequent to the appearance thereof, determines an average blood pressure based on said maximum and minimum blood pressures, one of said maximum, minimum and average blood pressures being used as said first blood pressure.

6. The apparatus as set forth in claim 5, wherein said second blood pressure measuring means determines, as a maximum blood pressure of said subject, a value of said fluid pressure when amplitudes of pulses of said oscillatory pressure wave are significantly largely increased. determines as a minimum blood pressure of said subject a value of said fluid pressure when the amplitudes of said pulses are significantly largely decreased subsequent to the significantly large increase, and determines an average blood pressure based on said maximum and minimum blood pressures, one of said maximum, minimum and average blood pressures being used as said second blood pressure.

7. The apparatus as set forth in claim 1, wherein said judging means uses a difference between said first and second blood pressures as said degree of inequality between said first and second blood pressures, said first and second blood pressure measuring means determining said first and second blood pressures, respectively, at each of a plurality of measuring cycles while said subject is in a normal condition, said judging means determining said reference value based on a maximum difference among the differences between the first blood pressures and corresponding second blood pressures determined at said measuring cycles.

8. The apparatus as set forth in claim 1, further comprising a display device for displaying, as a normal blood pressure, a value determined based on at least one of said first and second blood pressures, unless said judging means judges said at least one of the first and second blood pressures to be abnormal.

9. The apparatus as set forth in claim 8, wherein said display device displays an indication of abnormality, if said judging means judges said at least one of the first and second blood pressures to be abnormal.

* * * * *